United States Patent
Luhadiya et al.

(10) Patent No.: US 7,504,536 B2
(45) Date of Patent: Mar. 17, 2009

(54) COMPOSITIONS COMPRISING CALCIUM CITRATE MALATE AND METHODS FOR MAKING THE SAME

(75) Inventors: Ashok Premchand Luhadiya, Cincinnati, OH (US); Timothy William Dake, Cincinnati, OH (US); Glenn Richard Hudepohl, Cincinnati, OH (US); Donald Brown Compton, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/893,783

(22) Filed: Aug. 17, 2007

(65) Prior Publication Data

US 2008/0064896 A1 Mar. 13, 2008

Related U.S. Application Data

(60) Provisional application No. 60/838,315, filed on Aug. 17, 2006.

(51) Int. Cl.
*C07C 55/00* (2006.01)
*C07C 51/42* (2006.01)

(52) U.S. Cl. ...................... 562/590; 562/593
(58) Field of Classification Search ........................ None
See application file for complete search history.

(56) References Cited

U.S. PATENT DOCUMENTS

| 5,186,965 | A | * | 2/1993 | Fox et al. ..................... 426/74 |
| 6,235,322 | B1 | | 5/2001 | Lederman |
| 6,569,477 | B2 | | 5/2003 | Lederman |
| 6,706,904 | B1 | | 3/2004 | Hartle et al. |
| 2004/0228950 | A1 | | 11/2004 | Christiansen |

FOREIGN PATENT DOCUMENTS

| CN | 1257062 A | | 6/2000 |
| EP | 0 781 756 A1 | | 7/1997 |
| EP | 781756 | * | 7/1997 |
| JP | 56-097248 | | 8/1981 |
| WO | WO 92/21355 A | | 12/1992 |

OTHER PUBLICATIONS

International Search Report received in connection with PCT/IB2007/053296, mailed on Jul. 18, 2008.

* cited by examiner

*Primary Examiner*—Karl J Puttlitz
(74) *Attorney, Agent, or Firm*—Adam W. Borgman; Kim William Zerby; Steven W. Miller

(57) ABSTRACT

A process for producing a calcium citrate malate composition by the steps of: combining a calcium source, a citrate source, a malate source and water to form a calcium citrate malate mixture. The mixture is reacted until reaching a peak temperature of from about 45° C. to about 70° C., and then cooled at a rate of from about 1° C./minute to about 4° C./minute to reach a final temperature of less than about 40° C. A calcium citrate malate precipitate is formed and then dried to obtain the calcium citrate malate composition.

51 Claims, No Drawings

COMPOSITIONS COMPRISING CALCIUM CITRATE MALATE AND METHODS FOR MAKING THE SAME

CROSS REFERENCE TO RELATED APPLICATIONS

This application claims the benefit of and priority to provisional application No. 60/838,315, filed on Aug. 17, 2006, which is hereby incorporated by reference herein.

FIELD OF THE INVENTION

Embodiments of the present invention generally relate to compositions comprising calcium citrate malate and methods for making the same.

BACKGROUND OF THE INVENTION

Calcium is a mineral that is helpful for building and maintaining strong bones and preventing bone diseases such as osteoporosis. Therefore, it can be important for individuals to consume a calcium-rich diet. While a variety of dairy products provide good sources of calcium, many individuals still find it difficult to get the calcium they need. One reason for this is that individuals often find it difficult to consume the amount of such foods needed to satisfy their recommended daily allowance of calcium. With milk in particular, many individuals enjoy consuming a glass of milk from time to time, but may find it challenging to consume the roughly three full glasses they need to satisfy their recommended daily allowance of calcium. This task can be made even more difficult if the individual suffers from one of a variety of dairy or lactose-related conditions, such as, for example, lactose intolerance.

Fortunately, there are numerous forms of calcium supplements available to today's consumers including calcium tablets, capsules and powders. However, many current forms of supplementation still leave something to be desired.

Calcium tablets and capsules often come in various dosage strengths which can provide consumers with flexibility in their dosage regimen. However, the calcium within such supplements is often not as bioavailable as thought to be by the consumer, thereby resulting in the consumer absorbing less calcium than anticipated. Moreover, some consumers may find it difficult, if not impossible, to swallow tablets and capsules. Such consumers are effectively prevented from using a tablet or capsule form of calcium supplementation and, therefore, must look for alternate forms of calcium supplementation.

Currently available calcium powders, and more particularly, calcium citrate malate powders, may be sprinkled onto foods or mixed into beverages to allow the consumer to control when and how much of the calcium supplement is added. However, there may still be attendant issues. Currently available calcium citrate malate powders often do not dissolve quickly, leaving the consumer waiting for the powder to dissolve before consuming the food or beverage to which the powder has been added. Additionally, currently available calcium citrate malate powders often do not dissolve completely, thereby forming undesirable lumps that can be unacceptable to the consumer. Moreover, many currently available powders can negatively affect the taste and/or texture of the food or beverage to which it is added, thereby further decreasing consumer satisfaction.

Therefore, there remains a need for a calcium composition that may be dissolved quickly and completely in a variety of foods and beverages, without negatively impacting taste or texture of the food or beverage, such that the composition may be easily consumed by a majority of the population.

SUMMARY OF THE INVENTION

The present invention relates to a process for producing a calcium citrate malate composition comprising the steps of: combining a calcium source, a citrate source, a malate source and water to form a calcium citrate malate mixture. The mixture is then reacted until reaching a peak temperature of from about 45° C. to about 70° C., and then cooled at a rate of from about 1° C./minute to about 4° C./minute to reach a final temperature of less than about 40° C. A calcium citrate malate precipitate is formed and then dried to obtain the calcium citrate malate composition.

In another aspect of the present invention at least a portion of the calcium source is selected from the group consisting of calcium hydroxide, calcium oxide, calcium carbonate and mixtures thereof.

DETAILED DESCRIPTION OF THE INVENTION

Embodiments of the present invention may generally relate to compositions comprising calcium citrate malate and methods for making the same.

A. Definitions

As used herein, the term "alkaline calcium source" refers to one or more calcium compounds selected from the group consisting of calcium hydroxide, calcium oxide, calcium carbonate, other calcium compounds containing at least one hydroxide group, and mixtures thereof.

As used herein, the term "calcium source" refers to one or more calcium compounds used in making calcium citrate malate compositions.

As used herein, the term "citrate source" refers to one or more citrate compounds used in making calcium citrate malate compositions including citric acid and salts thereof.

As used herein, the term "malate source" refers to one or more malate compounds used in making calcium citrate malate compositions.

As used herein, the term "citrate malate mixture" means a mixture of citrate and malate sources and water.

As used herein, the term "calcium citrate malate mixture" refers to the aqueous mixture formed by combining the calcium source, the citrate and malate sources, and water at any stage from the time the materials are combined until the calcium citrate malate is dried. This mixture may also contain other components.

As used herein, the term "calcium citrate malate slurry" refers to an aqueous mixture comprising solid particles of calcium citrate malate. A calcium citrate malate slurry may comprise a "calcium citrate malate precipitate."

As used herein, the term "composition comprising calcium citrate malate" may be used interchangeably with "calcium citrate malate composition" to refer to a dried calcium citrate malate product described herein.

As used herein, the term "calcium citrate malate" may be used interchangeably with the term "CCM"

As used herein, the term "comprising" means various components can be co-jointly employed in the methods and articles of this invention. Accordingly, the terms "consisting essentially of" and "consisting of" are embodied in the term comprising.

As used herein, the term "dissolution" means dissolving the calcium citrate malate composition in water.

As used herein, the term "dissolution rate" means how fast the calcium citrate malate dissolves in water.

As used herein, the term "peak temperature" means the highest temperature reached when the calcium source, the citrate and malate sources, and water are combined and the neutralization reaction is at or near completion As used herein, the term "final temperature" means, after reaching the peak temperature, the temperature at which cooling of the calcium citrate malate mixture is substantially stopped As used herein, the term "pore area" means the surface area of the pores within the calcium citrate malate composition particles as determined by mercury intrusion/extrusion porosimetry.

B. Compositions

Exemplary embodiments of the present invention may generally comprise calcium citrate malate compositions that exhibit one or more of the following characteristics. The calcium citrate malate compositions may have a pore area of at least about 30 $m^2/g$, and in one embodiment from about 30 $m^2/g$ to about 95 $m^2/g$, and in yet another embodiment from about 40 $m^2/g$ to about 95 $m^2/g$. Having a pore area of less than about 30 $m^2/g$ may result in slow dissolution of the powder, while having a pore area of greater than about 95 $m^2/g$ is difficult to produce and results in particles with limited structural integrity. Thus, a calcium citrate malate composition having a pore area of at least about 30 $m^2/g$ may be desired.

Additionally, embodiments of the calcium citrate malate composition may have a dissolution rate in water of at least about 92%, and in one embodiment at least about 95%, and in yet another embodiment at least about 97% in less than about 120 seconds, in one embodiment less than about 90 seconds, and in still another embodiment less than about 60 seconds. Having a dissolution rate of at least about 92% in less than about 120 seconds can help ensure that the calcium citrate malate composition dissolves quickly and completely when added to a food or beverage, thereby reducing the likelihood of the development of cloudiness or unsightly lumps that may be unappealing to consumers.

Moreover, embodiments of calcium citrate malate compositions herein may have, when dissolved in water at 0.6% by weight, a pH of about 8 or less, and in one embodiment about from about 5 to about 8, and in yet another embodiment from about 6 to about 7. If the pH of the calcium citrate malate composition is either too high or too low (e.g. greater than about 8 or less than about 5) then it may impart an unpalatable flavor to the food or beverage to which it is added.

Furthermore, the calcium citrate malate compositions may have a moisture content of about 15% or less, and in one embodiment from about 5% to about 15%, and in yet another embodiment from about 5% to about 10%, by weight of the calcium citrate malate composition. Having a moisture content that is either greater than about 10% or less than about 5% may result in a calcium citrate malate composition that lacks the rapid and complete dissolution characteristics.

The average particle size of embodiments of the calcium citrate malate may be from about 20 to about 150 microns and in one embodiment from about 40 to about 100 microns. Such a particle size can further ensure the calcium citrate malate compositions comprises the dissolution characteristics described previously.

In one embodiment, the calcium citrate malate composition exhibits at least two of the previously described characteristics, and in another embodiment at least three of the characteristics, while in still another embodiment, all of the characteristics, where at least one of the characteristics must be either pore area or dissolution rate.

Exemplary compositions according to the present invention may exhibit a molar ratio of citrate:malate of from about 30:70 to about 80:20, and in another embodiment from about 30:70 to about 60:40, any in yet another embodiment from about 35:65 to about 55:45 and in still another embodiment from about 35:65 to about 45:55. Similarly, compositions according to the present invention may exhibit a defined equivalents ratio, which is the equivalents of citrate plus malate, including both acid and salt forms thereof, divided by the equivalents of calcium ((3× moles citrate+2× moles malate)/2× moles of calcium). In one embodiment, the equivalents ratio may be from about 0.8 to about 1.2, and in another embodiment from about 0.9 to about 1.1, and in yet another embodiment from about 0.95 to about 1.05 and in still another embodiment from about 1.0 to about 1.05.

Furthermore, embodiments of the compositions described herein may contain at least about 15% calcium, and in one embodiment at least about 20% calcium, by weight of the calcium citrate malate composition.

Embodiments of the present invention may also provide a benefit associated with administration of a composition comprising calcium citrate malate to a mammal in need of such benefit, wherein the calcium citrate malate exhibits any one or more, with at least one being either pore area or dissolution rate, of: a pore area of at least about 30 $m^2/g$, and in one embodiment from about 30 $m^2/g$ to about 95 $m^2/g$, and in yet another embodiment from about 40 $m^2/g$ to about 95 $m^2/g$; a dissolution rate of at least about 92%, and in one embodiment at least about 95%, and in yet another embodiment at least about 97% in less than about 120 seconds, in one embodiment less than about 90 seconds, and in still another embodiment less than about 60 seconds; a pH of about 8 or less, and in one embodiment about from about 5 to about 8, and in yet another embodiment from about 6 to about 7; and, a moisture content of about 15% or less, and in one embodiment from about 5% to about 15%, and in yet another embodiment from about 5% to about 10%, by weight of the calcium citrate malate composition.

Benefits associated with administration of a composition comprising calcium citrate malate may include, but are not limited to, bone growth, bone strengthening and/or treatment of osteoporosis.

It will be understood by those skilled in the art that if desired, the calcium citrate malate compositions may include additional components. By way of example and not limitation, the calcium citrate malate compositions may additionally include minerals, such as magnesium, iron, zinc and copper, additional acids and/or salts, such as phosphate, or other components, such as sugars, sorbitol, boron, vitamins and the like. The addition of such components may be desired to provide additional supplementation or to enhance the flavor of the compositions without affecting the dissolution properties thereof. Those skilled in the art will understand how such additional components may be added to the calcium citrate malate compositions.

B. Processes

Exemplary processes described herein may be used to prepare calcium citrate malate compositions having the desired dissolution characteristics described previously. Generally, such processes may comprise the steps of:

combining a calcium source, a citrate source, a malate source and water to form a calcium citrate malate mixture;

reacting the calcium citrate malate mixture, increasing the temperature until reaching a peak temperature of from about 45° C. to about 70° C.;

cooling the calcium citrate malate mixture at a rate of from about 1° C./minute to about 4° C./minute to reach a final temperature of less than about 40° C., forming a calcium citrate malate precipitate; and drying the calcium citrate malate precipitate to obtain the calcium citrate malate composition.

Variations to these processes will become clear from the description below.

Preferably, at least a portion of the calcium source is selected from the group consisting of calcium hydroxide, calcium oxide, calcium carbonate, other hydroxide containing calcium compounds including but not limited to dicalciumhydroxy malate (U.S. Pat. No. 6,706,904 B1) and mixtures thereof. In one embodiment the calcium source comprises calcium hydroxide, calcium oxide, or mixtures there of. In another embodiment the calcium source comprises calcium hydroxide. These calcium sources may be desired since they can react with citric and malic acids to form highly supersaturated CCM solutions yielding CCM compositions with higher levels of calcium than may be achieved with some other non-citrate or non-malate calcium salts. Supersaturation can be a driving force for precipitation of the CCM from the calcium citrate malate mixture.

It is recognized that under certain processing conditions calcium salts of citrate or malate may also be included as part of the calcium source. These include, but are not limited to tricalcium citrate, calcium hydrogen citrate, and calcium malate. Usage of these salts may be limited by the need for them to effectively completely dissolve at some stage during preparation and mixing of the CCM mixture. If they do not effectively-completely dissolve, they could act as seed crystals to produce precipitates without the desired dissolution rate characteristics.

It is also recognized that limited amounts of other calcium salts, such as chloride, phosphate, and salts of other organic acids may be used as long as the levels used do not interfere with the desired dissolution characteristics.

Citrate sources acceptable for use comprise citric acid. In addition, calcium citrate salts may be included as part of the citrate source with the same limitations as described in their use as part of the calcium source.

Malate sources acceptable for use comprise malic acid. In addition, calcium malate salts may be included as part of the malate source with the same limitations as described in their use as part of the calcium source.

It is also recognized that limited amounts of other citrate or malate salts, such as citrate or malate salts of potassium, sodium, zinc, or magnesium may be used as long as the levels used do not interfere with the desired dissolution rate characteristics.

Combining the calcium source, citrate source, malate source, and water to create the CCM mixture may be accomplished using a variety of methods. One such method comprises mixing the citrate and malate sources in a portion of the water to create an aqueous citrate malate mixture, mixing the calcium source in a second part of the water creating an aqueous calcium mixture, then pumping the aqueous calcium mixture into a well mixed tank containing the aqueous citrate malate mixture. The amounts of water used to prepare the two aqueous mixtures may be adjusted as desired to facilitate processing, depending on particular process equipment being used and the particular calcium, citrate, and malate sources and their amounts. However, in one embodiment the aqueous calcium mixture may have a calcium concentration of from about 5% to about 25% by weight, and in another embodiment from about 8% to about 20% by weight. In one embodiment the aqueous citrate malate mixture may have a citrate plus malate concentration of about 15% to about 60% by weight, and in another embodiment from about 30% to about 50% by weight.

Another way to create the CCM mixture is to first prepare an aqueous citrate malate mixture, then add the calcium source to the aqueous citrate malate mixture using a device designed to incorporate powders into liquids such as a Triblender or Quadro Ytron XC Powder Disperser. Yet another way to create the CCM mixture is to first prepare an aqueous calcium mixture and an aqueous citrate malate mixture, then combine them by pumping each mixture simultaneously through a pipe containing an in-line static mixer. Other methods of mixing will be known to those skilled in the art.

Once the preparation of the calcium citrate malate mixture is complete, the calcium citrate malate mixture may have a calcium concentration of from about 4% to about 9% by weight, and in one embodiment from about 4.5% to about 8%, and in yet another embodiment from about 5% to about 6.5% by weight of the calcium citrate malate mixture.

Combining the calcium source, citrate source, malate source, and water to produce the calcium citrate malate mixture enables the calcium source to react with the citrate and malate sources. One type of reaction that can occur is a neutralization reaction between an alkaline calcium source and acid forms of citrate and malate. Other reactions that can occur are complexation reactions between solubilized calcium ions and citrate and malate ions that may form various soluble complexes.

Upon combining the calcium source with the citrate and malate sources to create the aqueous calcium citrate malate mixture, it may be desirable for the temperature of the mixture to increase until it reaches a peak temperature. The temperature of the calcium citrate malate mixture may be monitored to ensure the temperature reaches a peak temperature of from about 45° C. to about 70° C., and in one embodiment, from about 50° C. to about 60° C., and in still another embodiment from about 60° C. to about 70° C. If the peak temperature of the mixture does not reach at least about 45° C., precipitation of the calcium citrate malate, as described herein below, may be undesirably delayed. Likewise, if the peak temperature of the mixture reaches greater than about 70° C. the calcium citrate malate may precipitate too rapidly causing the resulting calcium citrate malate composition to lack the desired dissolution characteristics. Additionally, if the mixture reaches a peak temperature of about 60° C. or above, it may be desirable to limit the time that the mixture is above about 60° C. in order to limit the formation of slower dissolving calcium citrate malate precipitate Thus, in one embodiment, once a temperature of about 60° C. is reached, the reaction may be continued at temperatures above about 60° C. for about 120 seconds or less, and in one embodiment for about 60 seconds or less, and in yet another embodiment for about 30 seconds or less, and in still another embodiment for about 15 seconds or less.

For some alkaline calcium sources, including but not limited to calcium hydroxide, the neutralization reaction between the calcium source and acid forms of citrate and malate is exothermic, and thus the temperature of the calcium citrate malate mixture may increase while the neutralization reaction takes place. If the neutralization reaction is not sufficient to raise the temperature to the desired peak temperature, it may be necessary to supply additional heat to the mixture to reach the desired peak temperature. If the neutralization reaction generates too much heat, it may be necessary to remove heat from the mixture so that the desired peak temperature is not exceeded. Once the desired peak temperature is achieved, the calcium citrate malate mixture can be cooled. For example, if a jacketed tank is being used a coolant, such as cold water, can be pumped through the jacketed tank to cool the mixture. The calcium citrate malate mixture may be cooled at a rate of from about 1° C./minute to about 4° C./minute, until the temperature is less than about 40° C. Moreover, if the peak temperature of the calcium citrate malate mixture is from about 50° C. to about 60° C., then the cooling rate may be from about 1° C./minute to about 3° C./minute until the temperature is less than about 40° C., and in one embodiment from about 5° C. to about 40° C., in another embodiment from about 10° C. to about 35° C. and in yet another embodiment from about 25° C. to about 35° C. Similarly, if the peak temperature is from about 60° C. to about 70° C., the cooling rate may be from about 3° C./minute to about 4° C./minute until the temperature is less than about 40° C., and in one embodiment from about 5° C. to about 40° C., in another embodiment from about 10° C. to about 35° C. and in yet another embodiment from about 25° C. to about 35° C. At about the time the peak temperature is reached or afterwards, a calcium citrate malate precipitate can begin to form creating a calcium citrate malate slurry. The previously described pairings of peak temperatures and cooling rates can help ensure that the calcium citrate malate composition exhibits the desired dissolution characteristics.

Precipitation of the calcium citrate malate may be monitored to determine when the precipitation is sufficiently complete. One way of doing this is to measure the refractive index of the calcium citrate malate mixture using a refractometer. Commonly used refractometers typically can report the measurement using the Brix scale. The Brix value is related to the amount of dissolved solids in water. So, as the precipitation of the calcium citrate malate proceeds, the Brix value will decrease.

The Brix reading must be corrected for any non-calcium citrate malate components dissolved in the calcium citrate malate mixture, so that the corrected reading represents the amount of calcium citrate malate remaining in solution. This can be done by making a solution containing the non-calcium citrate malate components and measuring its Brix value. This then is the background Brix value for the calcium citrate malate mixture. The corrected Brix for the calcium citrate malate mixture is then calculated by subtracting the background Brix value from the measured Brix value of the calcium citrate malate mixture.

Precipitation of the calcium citrate malate in the slurry may be continued until the dissolved solids content is about 10 Brix or less, and in another embodiment about 5 Brix or less and in yet another embodiment about 4 Brix or less.

Once precipitation has reached the desired endpoint the calcium citrate malate mixture can be dried to produce the calcium citrate malate composition. One of several drying techniques known to those skilled in the art may be employed to reduce the moisture content of the calcium citrate malate slurry to within the desired ranges as set forth previously in order to obtain a composition comprising calcium citrate malate. For example, drying may be carried out using spray drying, forced air tray drying, fluidized bed drying and the like. While those skilled in the art will appreciate how to carry out each of the previously mentioned drying techniques, briefly, spray drying involves spraying small droplets of the slurry into a current of hot air in a large chamber to promote rapid evaporation of water from the droplets. Forced air drying may also be used which involves circulating hot air directly over and or through tray containing the precipitate to promote uniform drying. Additionally, fluidized bed drying involves blowing hot air through a semi-moist bed of material, causing the material to become suspended and fluidized. The air acts as both the drying and fluidizing medium.

Additionally, the calcium citrate malate precipitate may be optionally filtered to remove excess water prior to drying. Filtration of the calcium citrate malate precipitate generally involves pressure, vacuum, or centrifugal methods of separation.

The foregoing exemplary processes can be used to provide calcium citrate malate compositions having the characteristics previously described.

ANALYTICAL METHODS

Parameters used to characterize elements of the present invention are quantified by particular analytical methods. These methods are described in detail as follows.

Calcium Citrate Malate
1. Moisture
The moisture content of the calcium citrate malate composition measured as follows.
 a) 2 g of calcium citrate malate powder is spread on an aluminum sample dish in a Sartorius Moisture Analyzer (Model: MA 30) and heated to 140° C. for 15 minutes.
 b) The moisture of the heated sample is calculated by the Sartorius Moisture analyzer MA 30 as % w/w.
2. Calcium Content of Calcium Citrate Malate Composition
The calcium content of the calcium citrate malate composition is measured by Inductively Coupled Plasma Atomic Emission Spectrometric AOAC, $17^{th}$ ed. 2000, <990.08>
3. Citrate to Malate Molar Ratio
The ratio of citrate to malate is determined by AOAC $15^{th}$ ed., 1990, <986.13>
4. Particle size of Calcium Citrate Malate Composition:
The particle size of the calcium citrate malate powder is measured by ASTM B214.
5. Calcium Citrate Malate Composition Dissolution Rate Measurement Method
The calcium citrate malate dissolution rate in water is measured by the change in water conductivity with respect to time as described below.
Apparatus & Reagent:
Thermo Orion Model 555A pHuture MMS Meter
DuraProbe™ 4-Electrode Conductivity Cells-013005A
RO water
Magnetic stirrer—400 Hotplate/stirrer, VWR Scientific Products 986006, Serial no. 0722, Mfg. Troemner Inc, USA

| Stir bar | Weight | 12.0-16.0 gm |
|---|---|---|
| | Length | 2 inches |
| | Diameter | ⅜ inch |

600 ml Pyrex glass beaker having 500 ml marking.
Determination:
 a) Transfer 500 ml of RO water having a temperature of 25° C. to the Pyrex glass beaker.
 b) Place the stir bar into the beaker and place the beaker on the magnetic stirrer.
 c) Start Stirring and maintain at a speed of 200 RPM.
 d) Immerse the conductivity probe into the beaker.
 e) Measure the conductivity of water (Cw).

f) Weigh 2.0 g of the calcium citrate malate composition.
g) Transfer the composition to the beaker by sprinkling the composition in the center of the vortex in less than 5 seconds.
h) Start the timer after the composition addition is completed.
i) Measure the conductivity (Ct) at selected times (t) such as t=30, 60, 90, 120, 480 seconds.
j) Ensure that there is no undissolved calcium citrate malate composition remaining in the beaker.
k) Continue mixing until no suspended particles are visible.
l) Determine the conductivity of the water containing the dissolved calcium citrate malate composition. This is the final conductivity (Cf).

Note: All measurements are done at 25° C.

Calculation:

$$Dt = (Ct - Cw)/(Cf - Cw) \text{ where}$$

Dt=dissolution at time t, expressed as a %
Ct=conductivity at time t
Cw=conductivity of water before adding the calcium citrate malate composition
Cf=final conductivity 6. Pore Area:
Pore area is determined by using Mercury Intrusion/Extrusion Porosimetry.
Materials and Equipment:
Drying oven
Polystyrene or aluminum weigh dishes
Stainless steel spatulas
Penetrometer
Analytical Balance
Ultra high purity or pre-purified grade Nitrogen
Mercury (triple distilled purity)
Vacuum grease (Apiezon H)
High pressure fluid
Micromeritics mercury porosimeter (AutoPore)
Sample Preparation The calcium citrate malate composition is dried in a Pyrex Petri dish at 110° C. for 2 days.
Procedure:
a) Weigh 0.2 g of the calcium citrate malate composition using a weighing dish.
b) Transfer the powder to the penetrometer.
c) Seal and weigh the penetrometer.
d) Insert the penetrometer low pressure analysis port (up to 50 psia) and run the analysis.
e) Remove the penetrometer from the low pressure port and weigh the assembly.
f) Insert penetrometer in high pressure analysis port (up to 60,000 psia) and run the analysis.
g) The result provides a pore volume distribution from 360 to 0.003 μm, total pore area (sq. m/gm).
Reference: Micromeritics Analytics Services (MAS), Norcross, Ga. (US), catalog number 942/65000/03

EXAMPLES

Example 1

About 73.04 gm of citric acid and about 76.16 gm of malic acid are dissolved in about 258 ml of distilled deionized water in a 1 liter glass beaker using a Teflon coated magnetic stir bar for about 5 minutes or until the acid solution is clear. The beaker is immersed in a non-circulating water bath at 25° C. About 84 gm of calcium hydroxide is dispersed in about 250 ml of distilled deionized water in a 500 ml glass beaker with stirring to produce a calcium hydroxide slurry. The calcium hydroxide slurry is then quickly added to the acid solution to produce a calcium citrate malate mixture. The calcium hydroxide beaker is rinsed with about 60 ml of deionized water and is added to the calcium citrate malate mixture. The temperature of the calcium citrate malate mixture rises to about 64.8° C., with the temperature above about 60° C. for less than about 60 seconds. The mixture is then cooled in a water bath to about 33° C. in about 15 minutes to obtain a slurry comprising a calcium citrate malate precipitate. The slurry and resulting precipitate are stirred for about another 75 minutes. After the 75 minutes, the soluble solids content of the slurry is determined to be about 2.8° Brix, as determined by a hand held refractometer. The calcium citrate malate precipitate is diluted by adding about 400 ml of deionized water and is spray dried at an inlet temperature of about 163° C. and an outlet temperature of about 72° C. to obtain a calcium citrate malate composition.

The dried calcium citrate malate composition is determined to have a pore area of about 58 m$^2$/gm, a pH about 6.5, a dissolution rate of about 98.6% in about 90 seconds.

Example 2

About 73.04 gm of citric acid and about 76.16 gm of malic acid are dissolved in about 228 ml of distilled deionized water in a 1 liter glass beaker using a Teflon coated magnetic stir bar for about 5 minutes or until the acid solution is clear. The beaker is immersed in a non-circulating water bath at about 25° C. About 84 gm of calcium hydroxide is dispersed in about 260 ml of distilled deionized water in a 500 ml glass beaker with stirring to produce a calcium hydroxide slurry. The calcium hydroxide slurry is then quickly added to the acid solution to produce a calcium citrate malate mixture. The calcium hydroxide beaker is rinsed with about 100 ml of deionized water and is added to the calcium citrate malate mixture. The temperature of the calcium citrate malate mixture rises to about 61° C., with the temperature above about 60° C. for less than about 10 seconds. The mixture is then cooled in a water bath to about 33° C. in about 15 minutes to obtain a calcium citrate slurry comprising a calcium citrate malate precipitate. The slurry and resulting precipitate are stirred for about another 75 minutes. After the 75 minutes, the soluble solids content is determined to be about 2.4° Brix, as determined by a hand held refractometer. The calcium citrate malate slurry is vacuum filtered and the cake is dried in fluidized bed drier at 60° C. inlet temperature to a moisture content of 9.5% w/w. The dried composition is sieved through a #100 mesh screen.

The dried calcium citrate malate composition is determined to have a pore area of about 67.7 m$^2$/gm, a pH about 6.5, and a dissolution rate of about 97% in about 90 seconds.

Example 3

70 kg of citric acid and 73 kg of malic acid are dissolved in about 256 liters of water using a Liquefier and then transferred to a 1100 liter jacketed tank fitted with an 8 inch propeller agitator running at about 730 RPM. Separately, 80.5 kg of calcium hydroxide is mixed into about 228 liters of water creating a calcium hydroxide slurry. Since the exothermic reaction between the calcium hydroxide and the citric and malic acids could cause the temperature to exceed 60° C. when combining the two aqueous mixtures with the equipment being used, only about half of the calcium hydroxide slurry is initially added to the acid solution. The temperature of the mixture in the jacketed tank increases to about 43° C.

The mixture is then cooled to about 36° C. by running cold water through the tank jacket. The remainder of the calcium hydroxide slurry is then added to the mixture in the jacketed tank and the temperature increases to a peak temperature of about 58° C. About 60 liters of water is then used to flush the lines of calcium hydroxide and this is added to the jacketed tank. The mixture in the tank is then cooled to below 40° C. at an average cooling rate of about 1.5° C. The cooling is stopped when the temperature of the mixture reaches about 30° C. Mixing and precipitation continue until the dissolved calcium citrate malate solids content is reduced to about 3.6 Brix as determined using a hand held refractometer. The calcium citrate malate slurry is then spray dried to a moisture content of 8.5%.

The dried calcium citrate malate composition is determined to have a pore area of about 73.5 $m^2$/gm, a pH of about 6.8, and a dissolution rate of about 98% in about 60 seconds.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for producing a calcium citrate malate composition comprising the steps of:
   combining a calcium source, a citrate source, a malate source, and water to form a calcium citrate malate mixture;
   reacting the calcium citrate malate mixture until reaching a peak temperature of from about 45° C. to about 70° C.;
   cooling the calcium citrate malate mixture at a rate of from about 1° C./minute to about 4° C./minute to reach a final temperature of between about 10° C. and about 40° C., forming a calcium citrate malate precipitate; and
   drying the calcium citrate malate precipitate to obtain the calcium citrate malate composition.

2. The process of claim 1 wherein at least a portion of the calcium source is selected from the group consisting of calcium hydroxide, calcium oxide, calcium carbonate, other calcium compounds containing at least one hydroxide group, and mixtures thereof.

3. The process of claim 1 wherein the calcium source is selected from the group consisting of calcium hydroxide, calcium oxide, calcium carbonate, and mixtures thereof.

4. The process of claim 1 wherein the calcium source comprises calcium hydroxide.

5. The process of claim 1 wherein the citrate source comprises citric acid.

6. The process of claim 1 wherein the malate source comprises malic acid.

7. The process of claim 1 wherein the calcium citrate malate mixture reaches a peak temperature of from about 50° C. to about 60° C.

8. The process of claim 1 wherein the calcium citrate malate mixture reaches a peak temperature of from about 60° C. to about 70° C.

9. The process of claim 1 wherein the weight percentage of calcium in the calcium citrate malate mixture is from about 4% to about 9%.

10. The process of claim 1 wherein the weight percentage of calcium in the calcium citrate malate mixture is from about 4.5% to about 8%.

11. The process of claim 1 wherein the weight percentage of calcium in the calcium citrate malate mixture is from about 5% to about 6.5%.

12. The process of claim 1 wherein during the reacting step, the temperature of the mixture is above about 60° C. for less than about 2 minutes.

13. The process of claim 1 wherein during the reacting step, the temperature of the mixture is above about 60° C. for less than about 1 minute.

14. The process of claim 1 wherein during the reacting step, the temperature of the mixture is above about 60° C. for less than about 30 seconds.

15. The process of claim 1 wherein during the reacting step, the temperature of the mixture is above about 60° C. for less than about 15 seconds.

16. The process of claim 1 wherein the final temperature after cooling is between about 25° C. and about 35° C.

17. The process of claim 1 wherein the calcium citrate malate precipitate is separated from the mixture by filtering or centrifuging before drying.

18. The process of claim 1 wherein the drying is spray drying.

19. The process of claim 1 wherein the calcium citrate malate mixture before drying exhibits a soluble solids content of about 10 Brix or less.

20. The process of claim 1 wherein the calcium citrate malate mixture before drying exhibits a soluble solids content of about 5 Brix or less.

21. The process of claim 1 wherein the calcium citrate malate mixture before drying exhibits a soluble solids content of about 4 Brix or less.

22. The process of claim 1 wherein the calcium citrate malate composition exhibits a pore area of at least about 30 $m^2$/gram.

23. The process of claim 1 wherein the calcium citrate malate composition exhibits a pore area of at least from about 40 $m^2$/gram to about 95 $m^2$/gram.

24. The process of claim 1 wherein the calcium citrate malate composition exhibits a dissolution rate of at least about 95%, by weight of the calcium citrate malate composition, in less than about 120 seconds.

25. The process of claim 1 wherein the calcium citrate malate composition exhibits a dissolution rate of at least about 95%, by weight of the calcium citrate malate composition, in less than about 90 seconds.

26. The process of claim 1 wherein the calcium citrate malate composition exhibits a dissolution rate of at least about 97%, by weight of the calcium citrate malate composition, in less than about 60 seconds.

27. The process of claim 1 wherein the calcium citrate malate composition exhibits a pH of about 8 or less.

28. The process of claim 1 wherein the calcium citrate malate composition exhibits a pH of from about 5 to about 8.

29. The process of claim 1 wherein the calcium citrate malate composition exhibits a pH of from about 6 to about 7.

30. The process of claim 1 wherein the calcium citrate malate composition exhibits a moisture content of about 15% or less by weight.

31. The process of claim 1 wherein the calcium citrate malate composition exhibits a moisture content of from about 5% to about 10% by weight.

32. The process of claim 1 wherein the calcium citrate malate composition has at least about 15% by weight calcium.

33. The process of claim 1 wherein the calcium citrate malate composition has at least about 20% by weight calcium.

34. The process of claim 1 wherein the calcium citrate malate composition has a molar ratio of citrate:malate of from about 30:70 to about 80:20.

35. The process of claim 1 wherein the calcium citrate malate composition has a molar ratio of citrate:malate of from about 30:70 to about 60:40.

36. The process of claim 1 wherein the calcium citrate malate composition has a molar ratio of citrate:malate of from about 35:65 to about 45:55.

37. The process of claim 1 wherein the equivalents ratio between the calcium and the citrate and malate is about 0.8 to 1.2.

38. The process of claim 1 wherein the calcium citrate malate composition has a molar ratio of citrate:malate of from about 30:70 to about 60:40, has an equivalents ratio between the calcium and the citrate and malate is from about 0.9 to about 1.1, and has at least about 20% by weight calcium.

39. The process of claim 1 wherein the calcium citrate malate composition has a molar ratio of citrate:malate of from about 35:65 to about 45:55, has an equivalents ratio between the calcium and the citrate and malate is about 1.0 to 1.05, and has at least about 20% by weight calcium.

40. A process for producing a calcium citrate malate composition comprising the steps of:
   combining a calcium source, a citrate source, a malate source, and water to form a calcium citrate malate mixture;
   reacting the calcium citrate malate mixture until reaching a peak temperature of from about 50° C. to about 60° C.;
   cooling the calcium citrate malate mixture at a rate of from about 1° C./minute to about 4° C./minute to reach a final temperature of between about 10° C. and about 40° C., forming a calcium citrate malate precipitate; and
   drying the calcium citrate malate precipitate to obtain the calcium citrate malate composition.

41. The process of claim 40 wherein the calcium citrate malate composition has a molar ratio of citrate:malate of from about 30:70 to about 60:40, has an equivalents ratio between the calcium and the citrate and malate is about 0.95 to 1.05, and has at least about 20% by weight calcium.

42. The process of claim 40 wherein the calcium citrate malate composition has a molar ratio of citrate:malate of from about 35:75 to about 45:55, has an equivalents ratio between the calcium and the citrate and malate is about 1.0 to 1.05, and has at least about 20% by weight calcium.

43. The process of claim 40 wherein the calcium citrate malate composition exhibits a pore area of at least from about 40 $m^2$/gram to about 95 $m^2$/gram and exhibits a dissolution rate of at least about 97%, by weight of the calcium citrate malate composition, in less than about 60 seconds.

44. The process of claim 40 wherein the calcium citrate malate composition exhibits a pH of from about 5 to about 8.

45. The process of claim 40 wherein the calcium citrate malate composition exhibits a moisture content of about 15% or less by weight.

46. A process for producing a calcium citrate malate composition comprising the steps of:
   combining a calcium source, a citrate source, a malate source, and water to form a calcium citrate malate mixture;
   reacting the calcium citrate malate mixture until reaching a peak temperature of from about 60° C. to about 70° C.;
   cooling the calcium citrate malate mixture at a rate of from about 3° C./minute to about 4° C./minute to reach a final temperature of between about 10° C. and about 40° C., forming a calcium citrate malate precipitate; and
   drying the calcium citrate malate precipitate to obtain the calcium citrate malate composition.

47. The process of claim 46 wherein the calcium citrate malate composition has a molar ratio of citrate:malate of from about 30:70 to about 60:40, has an equivalents ratio between the calcium and the citrate and malate is about 0.95 to 1.05, and has at least about 20% by weight calcium.

48. The process of claim 46 wherein the calcium citrate malate composition has a molar ratio of citrate:malate of from about 35:75 to about 45:55, has an equivalents ratio between the calcium and the citrate and malate is about 1.0 to 1.05, and has at least about 20% by weight calcium.

49. The process of claim 46 wherein the calcium citrate malate composition exhibits a pore area of at least from about 40 $m^2$/gram to about 95 $m^2$/gram and exhibits a dissolution rate of at least about 97%, by weight of the calcium citrate malate composition, in less than about 60 seconds.

50. The process of claim 46 wherein the calcium citrate malate composition exhibits a pH of from about 5 to about 8.

51. The process of claim 46 wherein the calcium citrate malate composition exhibits a moisture content of about 15% or less by weight.

* * * * *